US012569131B2

(12) United States Patent
Grondin et al.

(10) Patent No.: US 12,569,131 B2
(45) Date of Patent: Mar. 10, 2026

(54) METHOD FOR DETERMINING AN INDICATION OF AN ACUITY LEVEL OF A USER

(71) Applicant: TILAK HEALTHCARE SAS, Paris (FR)

(72) Inventors: Elidia Grondin, Chatou (FR); Quentin Le Cavorzin, Saint CyrLécole (FR); Pauline Vivier, Paris (FR)

(73) Assignee: Tilak Healthcare SAS, Paris (FR)

( * ) Notice: Subject to any disclaimer, the term of this patent is extended or adjusted under 35 U.S.C. 154(b) by 616 days.

(21) Appl. No.: 17/919,437

(22) PCT Filed: Apr. 14, 2021

(86) PCT No.: PCT/EP2021/059702
§ 371 (c)(1),
(2) Date: Oct. 17, 2022

(87) PCT Pub. No.: WO2021/209519
PCT Pub. Date: Oct. 21, 2021

(65) Prior Publication Data
US 2023/0157534 A1 May 25, 2023

(30) Foreign Application Priority Data
Apr. 17, 2020 (WO) ................. PCT/EP2020/060934

(51) Int. Cl.
*A61B 3/02* (2006.01)
*A61B 3/032* (2006.01)
(Continued)

(52) U.S. Cl.
CPC ................................... *A61B 3/032* (2013.01)

(58) Field of Classification Search
CPC ....... A61B 3/103; A61B 3/032; A61B 3/1015; A61B 3/0033; A61B 3/107; A61B 3/024;
(Continued)

(56) References Cited

U.S. PATENT DOCUMENTS 5,206,671 A 4/1993 Eydelman et al.
5,880,814 A * 3/1999 McKnight .............. A61B 3/032
351/239
(Continued)

FOREIGN PATENT DOCUMENTS

CN 1706340 A 12/2005
CN 103793719 A 5/2014
(Continued)

OTHER PUBLICATIONS

PCT Third Party Observation; International Application No. PCT/EP2021/059702; International Filing Date: Apr. 14, 2021.
(Continued)

*Primary Examiner* — Dawayne Pinkney
(74) *Attorney, Agent, or Firm* — Greenberg Traurig, LLP; Christopher C. Bolten; Robert D. Ward

(57) ABSTRACT

A computer implemented method and corresponding computer program product and device determine an indication of a user's acuity level. The methods and devices facilitate performance of acuity tests in a decentralized manner while establishing a desired test accuracy irrespective of a particular type of device or display, to determine the indication in a reliable manner. A computer implemented method includes the steps of: performing an optical acuity test using a control unit in communication with a device display having a predefined resolution; and displaying the optical acuity test on the display. The displayed optical acuity test includes a graphical representation with a discontinuity and prompts the user to identify the discontinuity by providing (Continued)

a response. The control unit and display provide that the optical acuity test is adjusted by generating and displaying the discontinuity based on the response and based on anti-aliasing using one or more display pixels.

29 Claims, 3 Drawing Sheets

(51) Int. Cl.
*A61B 3/10* (2006.01)
*A61B 3/12* (2006.01)

(58) Field of Classification Search
CPC ......... A61B 3/036; A61B 3/0041; A61B 3/14; A61B 3/113; A61B 3/1225; A61B 3/02; A61B 5/16; A61H 5/00; G09B 17/04
USPC ........ 351/200, 201, 203, 205, 206, 209–211, 351/221, 222, 237–246; 600/558
See application file for complete search history.

(56) References Cited

U.S. PATENT DOCUMENTS

| | | | |
|---|---|---|---|
| 8,881,058 | B2 | 11/2014 | Ollivierre et al. |
| 9,820,643 | B2 | 11/2017 | Borden et al. |
| 2008/0309879 | A1* | 12/2008 | Hirji ...................... A61B 3/032 |
| | | | 351/239 |
| 2010/0195051 | A1 | 8/2010 | Murray et al. |
| 2012/0050685 | A1 | 3/2012 | Bartlett et al. |
| 2013/0128229 | A1 | 5/2013 | Huang |
| 2013/0141697 | A1 | 6/2013 | Berry |
| 2015/0150444 | A1 | 6/2015 | Bex et al. |
| 2015/0190048 | A1 | 7/2015 | Huang |
| 2015/0346987 | A1 | 12/2015 | Ren et al. |
| 2016/0078594 | A1 | 3/2016 | Scherlen |
| 2017/0053604 | A1 | 2/2017 | Li et al. |
| 2017/0181618 | A1 | 6/2017 | Steinmueller et al. |
| 2018/0108294 | A1 | 4/2018 | Kwon et al. |
| 2019/0258054 | A1* | 8/2019 | Yoon .................. G02B 27/0172 |
| 2020/0253471 | A1 | 8/2020 | Prevoo et al. |
| 2022/0061651 | A1* | 3/2022 | Carroll ................... G16H 40/67 |

FOREIGN PATENT DOCUMENTS

| | | | |
|---|---|---|---|
| CN | 105832283 | A | 8/2016 |
| DE | 102015204640 | A1 | 9/2016 |
| JP | S6185918 | A | 5/1986 |
| JP | 2007020919 | A | 2/2007 |
| JP | 2008005961 | A | 1/2008 |
| JP | 2014533587 | A | 12/2014 |
| WO | 98/18381 | A1 | 5/1998 |
| WO | WO-03057021 | A1 | 7/2003 |
| WO | 2010132304 | A1 | 11/2010 |
| WO | 2016198902 | A1 | 12/2016 |
| WO | WO-2017152649 | A1 | 9/2017 |
| WO | 2019/017785 | A1 | 1/2019 |
| WO | WO-2019179931 | A1 | 9/2019 |
| WO | WO-2021209519 | A1 | 10/2021 |

OTHER PUBLICATIONS

Bach, Michael, Anti-aliasing and dithering in the Freiburg Visual Acuity Test, Universitiits-Augenklinik. Elektrophysiologisches Labor, D-79106 Freiburg, Germany , revised Dec. 20, 1996; accepted Jan. 23, 1997, Citation #2.

Pishnamaz et al., Striped Circle Visual Acuity Chart; A Novel Visual Acuity Chart Based on the Landolt-C Chart, Medical Hypothesis, Discovery & Innovation Ophthalmology Journal, 2018, Citation #1.

Harmening, Wolf M. et al., Vernier acuity in barn owls, Vision Research, Jan. 10, 2007; Issue No. of Periodical: 47, Citation #3.

Bilhaut, David et al. «Un jeu video therapeutique debarque sur smartphone», Le Quotidien du Medecin. Oct. 19, 2017, pp. 1-2 (Cited in: Europe) (We took notice of said document on: Jan. 27, 2023).

Gutierrez-Martinez, Jose-Maria et al. "Smartphones as a Light Measurement Tool: Case of Study", Applied Sciences, 2017, 7, 616, pp. 1-18 (Cited in: Europe) (We took notice of said document on: Jan. 27, 2023).

König, Immanuel et al. "A new context: Screen to face distance", Authorized licensed use limited to: University College London. Downloaded at Jan. 24, 2023 at 13:20:15 UTC from IEEE Xplore. (Cited in: Europe) (We took notice of said document on: Jan. 27, 2023).

Li et al. "Look into My Eyes: Fine-grained Detection of Face-screen Distance on Smartphones", School of Electronic Engineering and Computer Science, Computer Science Department, Peking University, Dec. 13, 2016 (Cited in: Europe) (We took notice of said document on: Jan. 27, 2023).

Rahman, Khandaker Abir et al. "Person to Camera Distance Measurement Based on Eye-Distance", 2009 Third International Conference on Multimedia and Ubiquitous Engineering, pp. 137-141 (Cited in: Europe) (We took notice of said document on: Jan. 27, 2023).

Ravnik, Robert et al. "Interactive and Audiance Adaptive Digital Signage Using Real-Time Computer Vision", International Journal of Advanced Robotic Systems, 2013, vol. 10, 107, pp. 1-7 (Cited in: Europe) (We took notice of said document on: Jan. 27, 2023).

Ricci et al. "Standardized measurement of visual acuity", Ophthalmic Epidemiology, 1998, vol. 5, No. 1, pp. 41-53 (Cited in: Europe) (We took notice of said document on: Jan. 27, 2023).

The Geometric Behavior of Light Chapter 2, pp. 13-28 (Cited in: Europe) (We took notice of said document on: Jan. 27, 2023).

The Geometrical Optics Workbook Chapter 1 Introduction to Geometrical Optics, pp. 1-20 (Cited in: Europe) (We took notice of said document on: Jan. 27, 2023).

Third Party Observation for application number EP20190713722; Publication No. EP3768147, dated Jan. 27, 2021;10 pages.

Amsler, Marc, Earliest Symptoms of Diseases of the Macula, Brit. J. Ophthal., 37:521 (1953).

Bastawrous et al. "The Development and Validation of a Smartphone Visual Acuity Test (Peek Acuity for Clinical Practice and Community-Based Fieldwork," JAMA Ophthalmol., vol. 133(8):930-937 (Aug. 2015).

Extended European Search Report dated Aug. 18, 2014 in EP Patent Appl. Serial No. 18163352.0 (010001).

"How to convert lux to candela", RapidTables, accessed on May 31, 2024, accessed at https://www.rapidtables.com/calc/light/ how-lux-to-candela.html (Year: 2024).

International Search Report & Written Opinion dated Jun. 26, 2019 in Int'l PCT Patent Appl. Serial No. PCT/EP2019/056685 (011001).

International Search Report & Written Opinion dated Jun. 23, 2021 in Int'l PCT Patent Appl. Serial No. PCT/EP2021/059702 (021001).

Machacek, German Patent Document DE 102015204640 A1, Translation from ESPACENET (2016).

Pelli, et al., The Design of a New Letter Chart for Measuring Contrast Sensitivity, Clin. Vision Sci., 2(3):187-199 (1988).

Third Party Observation (2nd Submission) dated Feb. 2, 2023 in EP Patent Application Serial No. 19713722.7, 8 pages.

Third Party Observation dated Feb. 2, 2023 in EP Patent Application Serial No. 19713722.7, 4 pages.

* cited by examiner

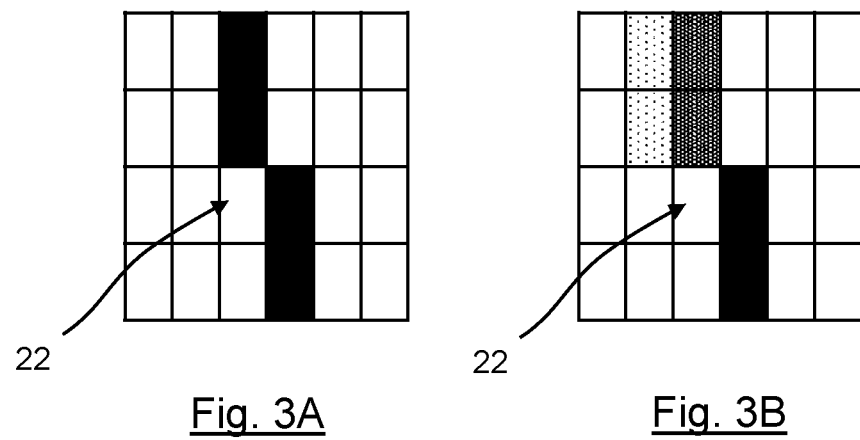
22
Fig. 3A                    Fig. 3B
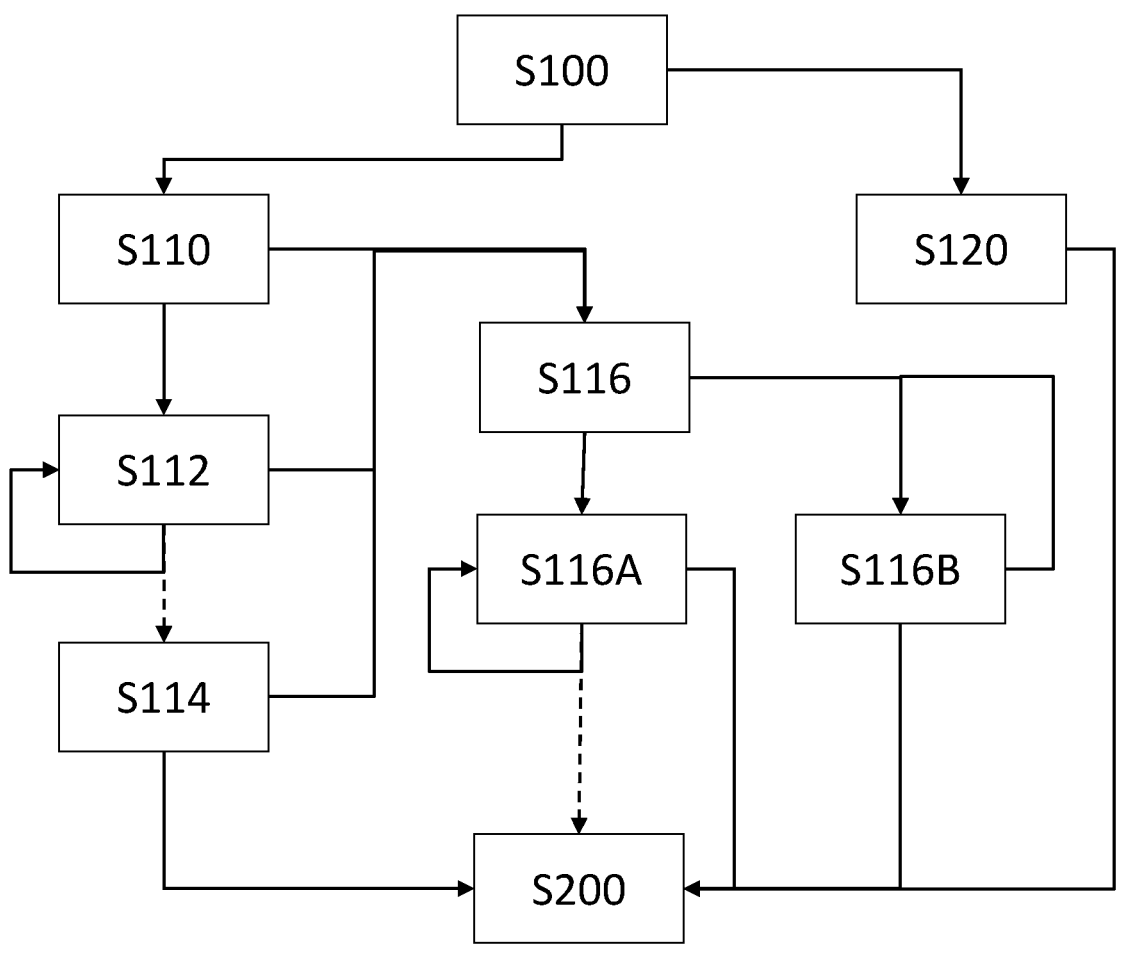
Fig. 4

METHOD FOR DETERMINING AN INDICATION OF AN ACUITY LEVEL OF A USER

CROSS-REFERENCE TO RELATED APPLICATIONS

This application is the U.S. National Stage of PCT/EP2021/059702 filed on Apr. 14, 2021, which claims priority to PCT Patent Application PCT/EP2020/060934 filed on Apr. 17, 2020, the entire content of both are incorporated herein by reference in their entirety.

FIELD OF THE INVENTION

The invention relates to the field of computer implemented methods for determining an indication of an acuity level of a user and a corresponding computer program product and a device.

BACKGROUND OF THE INVENTION

A large number of eye diseases exist, which may either be acquired due to visual behavior or physiological conditions or may at least in part be congenital, such that persons may be predisposed to develop a particular eye disease. In many of such instances, early diagnosis of a potential risk factor or developing eye disease may be essential so as to stall the development, improve the eye condition and/or cure the particular disease. For example, early diagnosis may result in an appropriate correction or medical therapy to reduce or remedy the experienced symptoms.

In order to assess the eye health, patients or people at risk of developing an eye disease are hence required to visit a medical professional such as an optometrist, wherein one or more tests may be performed to assist in assessing the eye condition and the patient's visual performance. Such visits to a physician's office or practice or medical institution may put a burden on the patient, in particular when the patient is required to perform such tests on a regular or periodical basis to track the development of the eye disease and/or the visual capacity of the patient.

Accordingly, it is preferred to perform such tests at a remote location, preferably at a patient's home. Whereas such tests are generally performed in a physician's practice on larger devices wherein both the patient and the device are at a particular position, such devices are absent at the patient's home. Therefore, the number of tests that may be performed at the remote location may be restricted to the available tools, which are—due to logistics and manufacturing costs—limited, thereby also putting constraints on the variability of such tests.

As an alternative, particular tests may be performed on computer or on devices capable of performing the required test, wherein a user may perform the test using a display of such device. However, as both the type of device and the ambient conditions may vary, it is generally difficult to ensure that the test is performed under equal and/or standard conditions. Currently, a user may only be provided with instructions to motivate the user to perform the test under the appropriate conditions and according to prescribed dimensions.

A number of eye diseases is related to the visual acuity, which is also referred to as the clarity of vision and is dependent on optical and neural factors, wherein low visual acuity may be due to refractive errors, such as aberrations in the shape of the eyeball or the cornea, astigmatism, and/or reduced flexibility of the lens. Such refractive errors may result in a nearsightedness or farsightedness of the user or patient. Furthermore, retinal diseases such as, for example, age related macular degeneration, may also be a cause of reduced acuity.

In order to assess the visual acuity, tests are generally performed while fixating and focusing the eye so as to provide a measure of central or foveal vision, as acuity is normally highest along the center. In addition, such tests may be based on the principle of Vernier acuity, which is a measurement of visual acuity that assesses the ability to discern the offset between two graduation segments sliding parallel to each other. When performing such tests, it is hence of importance to maintain a particular distance between the eye of the patient and the testing device, e.g. a display of a device, so as to ensure that the test is performed under the appropriate conditions and according to prescribed dimensions. That is considered critical, as the type of device may vary and the test conditions including the surroundings and the user's behavior may be inconsistent. By the same token, displays of various devices may have different characteristics and, in particular, may have varying resolutions, such that the tests may not be performed according to a common standard or under standardized conditions. Furthermore, an accuracy or assessing of the acuity level of such tests may furthermore be limited.

From WO 98/18381 A1 a visual acuity tester is known, which uses anti-aliasing to explicitly avoid any aberrations or distortions of standardized characters displayed on a customized display screen. In particular, the anti-aliasing is used for test characters by smoothing out the jagged edges that arise due to the inability of the ideal test character shape to be accommodated within the pixel array. Accordingly, the characters are displayed such that the user does not recognize any noticeable distortions and the characters are provided in a clear and centered manner so as to improve the appearance.

A further problem is lack of intuitiveness when actually performing the test, since such tests generally require that the user performs manual adjustments to correct for any displayed misalignments. Such manual adjustments may require the actuation of one or more buttons and may be time consuming and are hence not perceived as being user friendly. In addition, the risk of manual error is increased when performing the test under such conditions. Furthermore, manual adjustments may render it difficult to maintain conditions that are appropriate for performing the test, in particular since such tests are often time consuming.

Accordingly, there is a need for methods and devices to facilitate the performance of acuity tests in a decentralized manner while establishing a desired test accuracy, irrespective of a particular type of device so as to determine an acuity level of a user in a reliable manner.

SUMMARY OF THE INVENTION

It is an object of the present invention to provide a method and device for determining an acuity level of a user which improve the above undesirable problems.

Said object is achieved by the subject matter disclosed herein. Preferred embodiments are disclosed in the description, and the Figures.

Accordingly, in a first aspect, a computer implemented method for determining an acuity level of a user is suggested, which comprises the steps of performing an optical acuity test using a control unit being in communication with a display of a device, wherein the display has a predefined resolution; and displaying the optical acuity test on the display of the device, wherein the displayed optical acuity test comprises a graphical representation comprising a discontinuity and prompts the user to identify said discontinuity by providing a user response, wherein, using the control unit and the display, the optical acuity test is adjusted by generating and displaying the discontinuity based on the user response and based on anti-aliasing using one or more pixels of the display.

The use of the anti-aliasing enables that the range of possible discontinuities and hence the range of acuity levels to be measured may be increased. Accordingly, the discontinuity is generated and displayed based on anti-aliasing using one or more pixels of the display and using the control unit and the display.

Such anti-aliasing is based on the fact that pixels may not only be presented in black or white color, but may essentially comprise or exhibit any particular grayscale color therein between.

Although a user may more easily perceive a pixel shift of a black pixel, i.e. moving a black pixel towards an adjacent pixel and presenting the previous pixel position as a white pixel, he may not perceive a gradient shift, wherein e.g. a previously black pixel is reduced to 90 percent intensity and wherein an adjacent white pixel is increased to a black pixel intensity having a 10 percent pixel intensity. In other words, whereas in the first case a user may detect the pixel shift as a traversing pixel, he may not notice such gradient shift.

In particular for lines having a particular pixel thickness, e.g. 4 to 6 or 5 pixels, anti-aliasing may provide that an offset between such lines may not only be provided by full pixels, but by providing a gradient shift, wherein not only the outer pixels may contribute to such gradient shift, but also the pixels arranged more centrally may exhibit such gradient shift. Thereby, the accuracy and detail level of the acuity test may be further increased, such that support for medically significant acuity levels may be provided that were previously not identifyable using a standard display and using full pixel shifts.

Providing a discontinuity based on anti-aliasing may hence be considered as deliberately providing a deviation or (gradient) shift of a region of a structure of the graphical representation which may preferably be indicative of a particular acuity level, wherein the anti-aliasing enables an improved acuity testing resolution.

In addition, the resolution of the display is taken into account, such that the displayed acuity test may have varying dimensions depending e.g. on the size of the display and the pixel density. Therefore, the acuity test may be performed on a variety of devices without significantly modifying the appearance to a user.

For example, the computer implemented method may be performed on a laptop computer, notebook, tablet, or other portable hand-held device such as e.g. a mobile terminal or PDA, wherein the method may be implemented in a module or may be stored as computer-readable instructions stored on or otherwise provided to the device. Such instructions may then be executed by a control unit of the device, which, in certain embodiments, may be provided as a processor or integrated microprocessor, preferably communicatively coupled to an on-board memory and/or storage medium.

As outlined in the above, the display furthermore comprises or exhibits a resolution, which may be defined as a pixel density multiplied by the size or area of the display, wherein the area is defined by an extension of the display in a longitudinal direction of the device and a direction perpendicular to the longitudinal direction, e.g. a height and width of the display. Knowing the resolution of the display, the control unit may hence adjust or adapt the displayed acuity test so as to display the acuity test according to predefined dimensions.

The adaptation of the acuity test is not limited to a particular type of acuity test and may be implemented e.g. both when performing a test based on Vernier acuity and when testing variations in shapes. In either instance, the anti-aliasing provides that the accuracy and detail level of the acuity test may be further increased by providing gradient shifts rather than full pixel shifts.

The term "adjusting" is to be understood as including both an initial setting of the display and changing said settings during the performance of the acuity test, e.g. based on a user response. The adjusting or setting may be performed by providing a corresponding display or control signal to the display or display unit, thereby enabling the display to present the acuity test according to predefined dimensions.

When referring to predefined dimensions, it will be understood that the displayed acuity test may comprise a particular size and/or extension in at least one direction of the display. As described in the above, the control unit may output a control signal to the display—to e.g. increase the size or extension of the displayed acuity test, such that the acuity test may be displayed on only a portion of the display or extend over the display until essentially covering the entire display. The varying spanning furthermore depends on the resolution of the display, such that a display having a lower resolution may require a lower number of pixels to be activated compared with a display having a higher pixel density.

In order to further optimize the user's experience when performing the test, the displayed optical acuity test preferably comprises or essentially consists of a graphical representation displayed in black color on a white background. Such a feature, not only provides that the graphical representation is easily recognizable, but also reduces the perception of glare from ambient. In other words, even under conditions with strong ambient light, a user may still be able to see the graphical representation and is able to perform the acuity test without requiring considerable efforts that potentially render performing the acuity test difficult or strenuous.

The method enables performing various types of optical acuity tests, wherein the dimensions of the displayed acuity test may be accordingly adapted based on the resolution of the display. Preferably, the displayed optical acuity test comprises at least two lines, wherein the adjustment includes adjusting a size, length, and/or thickness of said lines. Accordingly, said lines may have the same overall appearance between a variety of devices having different resolutions.

For example, although the thickness of the lines may also consist of a predetermined number of pixels (e.g. 5 pixels), the width or thickness of the lines may be accordingly adapted such that e.g. (ultra) high resolution displays may use a larger number of pixels compared with displays having low resolutions, such that the thickness perceived by a user is essentially the same.

When performing the optical acuity test, the displayed optical acuity test comprises a graphical representation comprising a discontinuity and prompting the user to identify said discontinuity by providing a user response. Based on the user response, the optical acuity test may then be adjusted using the control unit.

The discontinuity may e.g. be provided as an irregularity of a shape, wherein the irregularity may be formed as an offset to a continuous line, e.g. by a circle having a bump or gap having a particular size or by two lines that arranged along a longitudinal axis, wherein said lines are offset in a perpendicular direction. Whereas larger discontinuities may more easily be identified by a user, smaller discontinuities may be less apparent and hence form a measure to determine the acuity level of the user. Based on the user responses, i.e. whether or not the user has correctly identified the discontinuity, the control unit may evaluate the user responses and determine the acuity level based e.g. on a scoring and/or averaging algorithm.

To further facilitate the interaction with the user performing the acuity test, the discontinuity is preferably aligned along a longitudinal direction of the display, wherein a user response is received by the control unit by a selection of an indication relating to the discontinuity, wherein the graphical representation comprises an indication on opposing ends of the graphical representation.

For example, rather than performing an adjustment or correction of a displayed misalignment, the user is merely required to indicate whether a discontinuity is present or not, such that the performance of the acuity test is facilitated and more intuitive, thereby improving the user experience and reducing the time required to perform the acuity test. Furthermore, this may also motivate a user to increase the frequency of performing such tests, such that the tests are more likely to be performed according to a prescribed interval. Thereby, it becomes more likely that the onset of e.g. macular degeneration or other factors that may influence or affect the acuity level of the user is detected at an earlier stage, such that a correction or medical treatment may be accordingly provided.

Having the indications at opposing ends furthermore ensures that the focus of the user is maintained in the center of the display, wherein the discontinuity is preferably displayed at the center. Thereby, any interfering objects and varying elements from the periphery of the device are screened out as much as possible and the display surrounding the graphical representation may be configured to provide a more homogenous appearance, when the user is performing the acuity test.

To further facilitate the user interaction and the performance of the acuity test, the display is preferably configured as a touchscreen, wherein the user response is received by the control unit by means of tactile interaction with the touchscreen at or in a direction of a region of the display corresponding to the indication. Such an approach ensures that the user may trigger the user response using interactions that may also be applied to other hand-held devices. The user may e.g. trigger the user response by means of tapping with a finger or swiping a finger from a central position on the display to the corresponding end comprising the indication. Thereby, no cumbersome adjustments are required and the user may maintain focused on the center of the display.

Furthermore, instead of e.g. detecting irregularities in shapes or selecting a shape having an irregularity compared with shapes having a continuous appearance, the graphical representation preferably comprises at least two lines. The at least two lines essentially arranged along a longitudinal direction of the display, wherein the discontinuity is formed as an offset of said lines in a direction perpendicular to the longitudinal direction of the display. As described in the above, the lines may hence be aligned essentially along the same axis so as to form a continuous line, yet are offset to each other starting from the connecting ends, i.e. in a staggered manner. In such case, the user may be required to indicate whether the lines form a continuous line or are discontinuous, wherein the displayed offset is a measure for the acuity level of the user.

Accordingly, it is preferred that the indication of the acuity level of the user is determined using the control unit and based on the user response.

To determine the indication of the acuity level, the acuity test may be performed by the control unit in two steps, wherein, in the first step, an indication of the initial acuity level is determined and, in the second step, said initial acuity level is refined and/or confirmed as an indication of a final acuity level. In other words, the first step may provide an estimate of the acuity level, whereas in the second step, a more exact test or fine-tuning of the indication of the acuity level is performed so as to resolve a final score or indicated acuity level. This has the advantage that the first step may be performed more rapidly while at the same time the two steps may be separated, i.e. be performed at different time points. This may be perceived as more comfortable, since the test is less time consuming and separation of the two steps may be less tiresome as the concentration timespan may be shortened.

The acuity test generally does not provide a diagnosis, although the result may be used as an acuity estimation and may obviate further tests. Instead, the acuity test generally provides an indication for a physician to assess the acuity performance to support performing a diagnosis.

In a preferred embodiment, in the first step, the graphical representation comprises a discontinuity corresponding to a first acuity level. If the user response correctly identifies the discontinuity, the control unit adjusts the acuity test by displaying on the display a further graphical representation comprising a discontinuity corresponding to a second acuity level and prompting the user to identify said discontinuity by providing a user response, the second acuity level being higher than the first acuity level. If the user response does not identify the discontinuity, the control unit sets the indication of the initial acuity level to a predefined initial acuity level being lower than the first acuity level.

The acuity level may be scored with reference to the Logarithm of the Minimum Angle of Resolution, also known as LogMAR values. Using such a scaling, it is considered that an observer who can resolve details as small as 1 minute of visual angle scores LogMAR 0, since the base-10 logarithm of 1 is 0. By the same token, an observer who can resolve details as small as 2 minutes of visual angle scores LogMAR 0.3, since the base-10 logarithm of 2 is near-approximately 0.3, wherein the higher value indicates a corresponding reduced visual acuity. Using the discontinuity, an offset in the graphical representation may hence correspond to a particular LogMAR value, such that starting from a first acuity level corresponding to e.g. a LogMAR value of 0.7, graphical representations comprising a continuity with increasing acuity levels may be displayed, ranging e.g. up to LogMAR−0.7. Should the user be unable to identify the first acuity level, the indication of the initial acuity level or estimate threshold may be set to a lower acuity level, e.g. LogMAR 1.0.

On the other hand, if the user response correctly identifies the discontinuity according to the second acuity level, the method further may comprise performing the step of adjusting the acuity test by displaying, using the control unit, on the display a further graphical representation. It may comprise a discontinuity corresponding to an acuity level being higher than the previous acuity level with a predefined amount and prompting the user to identify said discontinuity by providing a user response. Said step is typically repeated until a predefined maximum acuity level is achieved, if the user response correctly identifies the discontinuity, thereby achieving an indication of the initial acuity level, or until the user response does not identify the discontinuity.

Following the above example, a user may be presented with a discontinuity corresponding to a first acuity value of LogMAR 0.7. After having identified the discontinuity, the subsequent graphical representations that are displayed comprise a reduced LogMAR value, i.e. having a higher acuity value, with a predefined amount, such that the second graphical representation may correspond to a LogMAR value of e.g. 0.4 and wherein the predefined amount or Δ value is 0.3. By the same token, should the discontinuity according to the second graphical representation be correctly identified, a third graphical representation is displayed, wherein the discontinuity is adjusted so as to obtain a LogMAR value of 0.1, and so on, until a predefined maximum LogMAR is achieved of, for example, −0.7. The predefined amount may vary between each step, such that e.g. a first set of graphical representations may correspond to larger visual acuity differences and differences between discontinuities towards the maximum LogMAR value are smaller, so as to provide an improved estimate of the initial acuity level.

However, if the user response does not identify the discontinuity, e.g. the second or subsequent discontinuity, the method may further comprise performing the step of adjusting the acuity test by displaying, using the control unit, on the display a further graphical representation. The further graphical representation may comprise a discontinuity corresponding to an acuity level being lower than the previous acuity level with a predefined amount and prompting the user to identify said discontinuity by providing a further user response, wherein if the further user response does not identify the discontinuity, said step is repeated until a discontinuity is correctly identified, until the first acuity level is achieved, or until a total of two subsequent discontinuities have not been identified, wherein the indication of the initial acuity level is set to the acuity level corresponding to the last displayed discontinuity; or if the further user response identifies the discontinuity, the method further comprises performing the step of adjusting the acuity test by displaying, using the control unit, on the display a further graphical representation comprising a discontinuity corresponding to an acuity level being higher than the previous acuity level with a predefined amount and prompting the user to identify said discontinuity by providing a further user response, wherein, if the further user response identifies the discontinuity, said step is repeated until a discontinuity is not identified or until the maximum acuity level is achieved, wherein the indication of the initial acuity level is set to the acuity level corresponding to the last displayed discontinuity.

Again, following the above example based on LogMAR values, the second acuity level may e.g. correspond to a LogMAR value of 0.4. Should said discontinuity not be identified, the control unit may increase the LogMAR value by a predefined Δ value of, for example, 0.2, such that the subsequent discontinuity that is displayed corresponds to a LogMAR value of 0.6. By the same token, should the user identify e.g. the second and third discontinuity, the third discontinuity corresponding to a Δ value of e.g. −0.1, and does not identify the fourth discontinuity having a LogMAR value of e.g. 0.4, the control unit increases the LogMAR value by a predefined Δ value of e.g. +0.1, such that the display displays a further graphical representation having a LogMAR value of 0.5.

In such a scenario, there are two options. If the user does not identify the discontinuity, further graphical representations are subsequently displayed prompting the user to identify the discontinuity, wherein the LogMAR value of each subsequent discontinuity is increased by a predefined amount or Δ value. This sequence is stopped, once a discontinuity is correctly identified or until the first acuity level is achieved. For example, if the graphical representation having a LogMAR value of 0 is not identified, the next discontinuity may correspond to a LogMAR value of 0.1. If the user identifies said discontinuity, the indication of the initial acuity level is set to a LogMAR value of 0.1. However, if the user does not identify any of the subsequent discontinuities and the first acuity level of e.g. 0.7 is reached, the control unit will set the indication of the initial acuity level to the first acuity level.

Alternatively, to reduce potential error and to speed up the acuity test, i.e. the first step of the acuity test, the indication of the initial acuity level may also be set to the acuity level corresponding to the previously displayed discontinuity, once a total of two discontinuities, preferably subsequent, have not been identified.

The second option provides that the acuity test is adjusted, if the further user response identifies the discontinuity, by displaying a further graphical representation comprising a discontinuity corresponding to an acuity level being higher than the previous acuity level with a predefined amount and prompting the user to identify said discontinuity by providing a further user response. For example, the initial increase in the LogMAR value up to e.g. 0 may be identified by the user, wherein the subsequently displayed graphical representation comprises a discontinuity corresponding to a LogMAR value of −0.1, e.g. wherein lowering of the LogMAR value is performed with a predefined amount or Δ value of 0.1. This step both provides an initial finetuning and a reduction of any potential statistical error. If the user identifies the subsequent discontinuity, said step is repeated until a discontinuity is not identified, e.g. corresponding to a LogMAR value of −0.3, wherein the indication of the initial acuity level is set to the acuity level corresponding to said value. By the same token, should the user reach the maximum acuity level, e.g. corresponding to a LogMAR value of −0.7, the indication of the initial acuity level is set to the acuity level corresponding to the maximum LogMAR value.

After having obtained the indication of the initial acuity level, the method may perform the second step, wherein a pool of graphical representations is generated, each graphical representation comprising a discontinuity corresponding to a specific acuity level. The pool typically comprises a predefined number of graphical representations having a discontinuity according to the indication of the initial acuity level and further comprises a predefined number of graphical representations having a discontinuity corresponding to an acuity level being higher than the indication of the initial acuity level with a predefined amount, i.e. corresponding to a lower LogMAR value. The acuity test is adjusted by displaying, using the control unit, on the display a randomly selected graphical representation from said pool and by prompting the user to identify said discontinuity, wherein the method comprises the step of adding a predefined number of graphical representations having a discontinuity corresponding to an acuity level being higher than the indication of the initial acuity level with a predefined amount, if the further user response identifies the discontinuity and if a graphical representation having a discontinuity corresponding to said acuity level has not yet been added to the pool and does not exceed a predefined amount from the indication of the initial acuity level; and/or adding a predefined number of graphical representations having a discontinuity corresponding to an acuity level being lower than the indication of the initial acuity level with a predefined amount or equal to the indication of the initial acuity level, if the further user response does not identify the discontinuity and if a graphical representation having a discontinuity corresponding to said acuity level has not yet been added to the pool and does not exceed a predefined amount from the indication of the initial acuity level, wherein the graphical representations are subsequently displayed and wherein each displayed graphical representation is removed from the pool, once a user response has been received, and wherein an indication of the final acuity level is determined based on the user responses.

The indication of the initial acuity level may be obtained corresponding to e.g. a LogMAR value of −0.3. In this case, the pool is generated by including a predefined number, e.g. three, graphical representations having a discontinuity corresponding to −0.3. Furthermore, the pool includes a predefined number of graphical representations having a discontinuity with a higher acuity level, wherein the predefined amount may correspond to e.g. a LogMAR delta value of 0.1, such that a predefined number, e.g. also three, of graphical representations having a discontinuity corresponding to −0.4 is added to the pool. The predefined numbers, although this may be provided in an embodiment, are merely provided for exemplary purposes and may be different for each group of graphical representations or acuity level. By the same token, the predefined amount may also correspond to higher or lower values, depending on the desired accuracy of the acuity level to be determined.

After said pool is generated, a random graphical representation is displayed and the user is prompted to identify said graphical representation. In this case, the user may either correctly identify the discontinuity or may perceive the discontinuity e.g. as a continuous graphical representation. In the former case, a predefined number of graphical representations having a discontinuity corresponding to an acuity level being higher than the indication of the initial acuity level with a predefined amount is added to the pool. However, this is only the case, if a graphical representation having a discontinuity corresponding to said acuity level has not yet been added to the pool and the level does not exceed a predefined amount from the indication of the initial acuity level.

In other words, should a randomly displayed graphical representation comprise a discontinuity corresponding to a LogMAR value of −0.4, a graphical representation having a discontinuity with a higher acuity level, e.g. corresponding to a LogMAR value of −0.5 does not exceed a predefined amount of e.g. 0.4 LogMAR, i.e. does not exceed −0.7 LogMAR or 1 LogMAR. Furthermore, after generation of the initial pool no graphical representations comprising discontinuities corresponding to said acuity level may have been added. Accordingly, a predefined number of graphical representations with discontinuities corresponding e.g. −0.5 LogMAR, i.e. corresponding to a higher acuity level are added to the pool. In the above example, the initial pool may comprise a total of six graphical representations, wherein three discontinuities correspond to a LogMAR value of −0.3 and three discontinuities correspond to a LogMAR value of −0.4. After identifying a discontinuity corresponding to a LogMAR value of −0.4, e.g. three further graphical representations are added to the pool having discontinuities corresponding to a LogMAR value of e.g. −0.5. Once the first displayed graphical representation has been removed from the pool, the pool consists of a total of eight graphical representations, wherein three discontinuities correspond to a LogMAR value of −0.3, three discontinuities correspond to a LogMAR value of −0.5 and now two discontinuities correspond to a LogMAR value of −0.4, for example.

This addition is performed, since no further graphical representations corresponding to the respective LogMAR value has yet been added to the pool and the higher acuity level did not exceed a predefined offset from the indicated initial acuity level. On the other hand, if a further displayed graphical representation also has a discontinuity corresponding to the LogMAR value of −0.3, no further graphical representations are added to the pool upon correct identification, since graphical representations with discontinuities having a higher acuity level have already been added.

If the further user response does not identify the discontinuity corresponding to e.g. to the LogMAR value of −0.4, a predefined number of graphical representations having a discontinuity corresponding to the indication of the initial acuity level, e.g. to a LogMAR value of −0.3 is not added, since graphical representations comprising corresponding discontinuities had already been added upon generation of the pool. On the other hand, if a further user response does not identify the discontinuity corresponding to e.g. to the LogMAR value of −0.3, a predefined number of graphical representations having a discontinuity corresponding to e.g. the LogMAR value of −0.2 is added, since such corresponding acuity levels had not yet been added and the acuity level does not exceed the predefined tolerance range, e.g. from −0.7 to 1 LogMAR.

After graphical representations have been displayed and the corresponding user responses have been received, the indication of the final acuity level is determined based on the user responses, when the pool comprises no further graphical representations. Preferably, the indication of the final acuity level corresponds to the last correctly identified highest acuity level or the indication of the final acuity level may be determined as the highest acuity level for which a majority of the user responses corresponds to an identification of the discontinuity. For example, if two out of three discontinuities corresponding to the same, highest acuity level have been correctly identified, said acuity level will be used as a final estimate or assessment of the acuity level. However, if a majority of the user responses does not correspond to an identification of the discontinuity, the indication of the final acuity level may be determined as the next acuity level, for which such majority has been determined.

Alternatively, or in addition, this may be done e.g. by evaluating the user responses and performing a statistical analysis and/or averaging a corresponding score defined by the respective user responses and corresponding acuity levels.

The generation of the pool preferably includes evaluating user responses of the predefined number of graphical representations having a discontinuity according to the indication of the initial acuity level, wherein the further predefined number of graphical representations have a discontinuity corresponding to an acuity level being higher than the indication of the initial acuity level with a predefined amount, if a majority of the user responses corresponds to an identification of the discontinuity, or to an acuity level being lower than the indication of the initial acuity level with a predefined amount, if a majority of the user responses does not correspond to an identification of the discontinuity. Accordingly, following the above example, the initial pool may be comprised of e.g. three graphical representations having a discontinuity according to the indication of the initial acuity level of −0.3 LogMAR and three graphical representations having a discontinuity corresponding to an acuity level of −0.4 LogMAR.

When performing the optical acuity test, it may furthermore be foreseen that the alignment of the graphical representation is switched to an alignment being perpendicular to the longitudinal direction or to an alignment, wherein the device is rotated from an upright position to a laterally extending position, when the second step is performed. In other words, the user may maintain the display in an upright position while performing the first step of the acuity test. The orientation of the graphical representations are automatically rotated or alternatively the user is requested to rotate the display by about 90 degrees when performing the second step. This ensures that the acuity is tested in at least two orientations and that a user may be incentivized and motivated to continue performing the acuity test due to variation of the orientation.

In order to maintain a predefined distance, the device may furthermore comprise an optical sensor and the method may provide that a warning is outputted, if a user is not within a predefined range, i.e. being too far away from or too close to the display.

More preferably, the method further comprises the step of detecting at least a facial characteristic of a user by means of an optical sensor of the device being in communication with the control unit, wherein the control unit determines a distance between the display and the detected facial characteristic of the user based on the detected facial characteristic and adjusts the displayed optical acuity test based on the determined distance and the resolution.

According to a preferred embodiment, the user is from about 35 cm to about 45 cm, preferably at about 40 cm from the display. Therefore, the user has to adapt its position relative to the display or remain at a stationary position at any time during the performance of the acuity test.

According to another embodiment, the determination of the distance between the display and the facial characteristic or face of a user allows automatic adaptation of the displayed acuity test on the display it is ensured that the user perceives the test in the appropriate dimensions. In other words, approximately the same acuity level may be determined at a variety of distances, such that any deviation from a prescribed distance may be accounted for. Thereby, the validity of the test is increased while at the same time the performance of the acuity test is simplified, i.e. a user does not continuously have to modify its position relative to the display or remain at a stationary position at any time during the performance of the acuity test.

The predefined dimensions correspond to the distance determined between the display and the face of the user. For example: Should the user change its position relative to the display, the control unit may accordingly increase the dimensions in at least one direction so as to ensure that the overall appearance of the acuity test remains essentially the same. When referring to predefined dimensions, it will be understood that the displayed acuity test may comprise a particular size and/or extension in at least one direction of the display. As described in the above, the control unit may output a control signal to the display—to e.g. increase the size or extension of the displayed acuity test upon an increasing distance between the user and the display, such that rather than being displayed on only a portion of the display, the acuity test may extend over the display until essentially covering the entire display, depending on the determined distance. The varying spanning furthermore depends on the resolution of the display, such that a display having a lower resolution may require a lower number of pixels to be activated compared with a display having a higher pixel density. Based on the determined distance to the user interacting with the device to perform the acuity test, the control unit of the device may hence adjust the displayed acuity test.

Although a facial characteristic is preferably detected by the optical sensor, e.g. a particular feature such as the eyes, nose, or overall shape using feature recognition, the optical sensor may also be configured to determine the presence of facial characteristics based on detected signals indicating a particular distance range, e.g. between 20 cm and 70 cm, a contrast level, an object size, and the like. The optical sensor may be composed of a plurality of sensor elements that are preferably arranged in an array and is preferably provided as a camera or camera sensor.

In addition to determining the distance or as an alternative, the displayed optical acuity test may furthermore be adjusted by the control unit based on an ambient brightness, contrast, and/or hue detected by the optical sensor or alternatively, the user can adjust these conditions accordingly.

For example, brightness and hue may vary throughout the day and furthermore depend on the surroundings of the user, e.g. whether the user is currently located in an indoor environment or is at an outdoor position. Furthermore, such ambient conditions may vary depending on both environmental factors, as the weather, and on a geographical position and angular position of the user with respect to e.g. the sun. According to a particular embodiment, the control unit may hence take said varying ambient conditions into account, such that an appearance of the displayed acuity test to a user may be adjusted accordingly and the displayed acuity test is hence essentially the same under varying ambient conditions.

Preferably, the adjustment includes adjusting luminosity, contrast, and/or hue of the display. For example, the control unit may transmit a control signal to the display indicating an increase in luminosity and implementing a hue with more blue tones, when the detected brightness is reduced, e.g. when the acuity test is performed in the morning or late afternoon rather than during mid-day. By the same token, the control signal may indicate an increase in contrast in case a high brightness is detected, for example, in the case of indoor lighting being turned on or when the acuity test is performed during mid-day rather than in the evening. Thereby, the overall appearance to a user is not significantly changed, such that the validity of the acuity test is further increased by maintaining and accordingly adapting the light conditions based on the experienced ambient lighting.

In the case of a hand-held device, the user may furthermore interact with the device in various positions, wherein the posture and interaction angle with the device may vary. For example, a user may use a laptop computer, which may be placed on a solid surface, yet the user may interact with the laptop from varying heights and at varying angles. By the same token, a mobile terminal may be held e.g. either at waist height or at chest or eye height, wherein the angle between the face of the user and the display may accordingly vary. Therefore, an angle between the display and the detected facial characteristic of the user is preferably determined using the control unit, wherein the displayed optical acuity test may be adjusted based on the determined angle. For example, the displayed acuity test may be displayed with a perspective according to the determined angle, wherein the extension of the displayed acuity test may be accordingly adjusted.

This furthermore increases the stability of the testing conditions, such that the acuity test may be performed essentially under standard conditions. Although the user may e.g. tilt the device, the displayed acuity test has a stationary appearance, such that the user always perceives the displayed acuity test in essentially the same manner.

The adjustment may be performed continuously or periodically. For example, any minor deviations in the signal detected by the optical sensor may be ignored based on a predefined threshold and/or may be evaluated over time so as to perform e.g. a periodic adjustment, if the deviation persists over a predefined period of time. Alternatively, the displayed acuity test may also be continuously adjusted, for example every second to every 5 to 10 seconds, wherein the adjustment rate may preferably be manually chosen depending on the user's preferences and/or the particular situation of the user.

In order to further optimize the user's experience when performing the test, the displayed optical acuity test preferably comprises or essentially consists of a graphical representation displayed in black color on a white background. Such a feature, not only provides that the graphical representation is easily recognizable, but also reduces the perception of glare from ambient. In other words, even under conditions with strong ambient light, a user may still be able to see the graphical representation and is able to perform the acuity test without requiring considerable efforts that potentially render performing the acuity test difficult or strenuous.

The method enables performing various types of optical acuity tests, wherein the dimensions of the displayed acuity test may be accordingly adapted based preferably on, both, the resolution of the display and the determined distance between the display and the user.

Preferably, the displayed optical acuity test comprises at least two lines, wherein the adjustment includes adjusting a size, length, and/or thickness of said lines. Accordingly, said lines may not only have the same overall appearance between a variety of devices having different resolutions, but also when the user is present at varying distances relative to the display.

For example, although the thickness of the lines may also consist of a predetermined number of pixels, the width or thickness of the lines may be accordingly adapted such that e.g. (ultra) high resolution displays may use a larger number of pixels compared with displays having low resolutions, such that the thickness perceived by a user is essentially the same. However, it may be provided that the thickness is not adjusted based on the determined distance. Hence, the thickness remains the same for every distance determined between the user and the display when performing the acuity test on the same device. In contrast, however, a length of the lines may be adapted according to the determined distance, such that the user perceives the acuity test in a similar or essentially identical manner at varying distances.

The above object is furthermore achieved by a computer program product embodied on a computer readable storage medium and configured so as when executed on a processor to perform operations of the computer implemented method as described in the above.

For example, the computer program product may be configured as a module stored in a memory of a device or otherwise being stored on e.g. a flash drive, SSD, or HDD, and may furthermore be embodied on a portable storage device.

The above object is furthermore also achieved by a device for determining an acuity level of a user, comprising a control unit, a display, and optionally an optical sensor, wherein the device is configured to perform the computer implemented method as described in the above.

Preferably, the device is configured as a portable and/or hand-held device, such that the user may carry the device and is hence facilitated to perform the method at any desirable remote location. Furthermore, this provides that the computer implemented method may be performed on a device of the user used for other purposes, such that no separate device is required to perform the method. Preferably, the device is configured as a mobile terminal, wherein an optical sensor may be implemented as an integrated camera. The camera is preferably a front camera in proximity of the display, such that a user is not required to rotate or turn around the mobile terminal to provide e.g. a periodic adjustment of the optical acuity test based on signals received by the camera. Furthermore, this also provides that a continuous adjustment of the test may be performed, such that optimized and standard conditions are established at any time during the performance of the optical acuity test.

The device may furthermore comprise a wireless communication module, wherein the control unit is configured to perform the optical acuity test using data received from said wireless communication module and/or to transmit the determined acuity level to a remote device using said wireless communication module.

For example, the optical acuity test may not or only be temporarily stored on the device, e.g. in a memory of the device, wherein the data or instructions required to execute or perform the optical acuity test are received via the wireless communication module, e.g. from a cloud server or network interface. Such an approach ensures that any updates of the optical acuity test are automatically implemented and that the required storage space on the device may be reduced or minimized. Alternatively, or in addition, the wireless communication module may enable that the determined acuity level may be automatically reported to e.g. a medical professional, such that the development of the visual acuity may be tracked and monitored. For example, the data may comprise the user responses and corresponding acuity levels, the determined indication of the initial acuity level, and/or the final acuity level, depending on the level of detail required to track and/or monitor the visual acuity development.

BRIEF DESCRIPTION OF THE DRAWINGS

The present disclosure will be more readily appreciated by reference to the following detailed description when being considered in connection with the accompanying drawings in which:

FIGS. 3A and 3B schematically depict a method for using anti-aliasing in a graphical representation comprising a discontinuity;

FIG. 4 schematically depicts steps for determining an indication of an initial acuity level according to a first step of an optical acuity test.

DETAILED DESCRIPTION OF PREFERRED EMBODIMENTS

Figure 1:
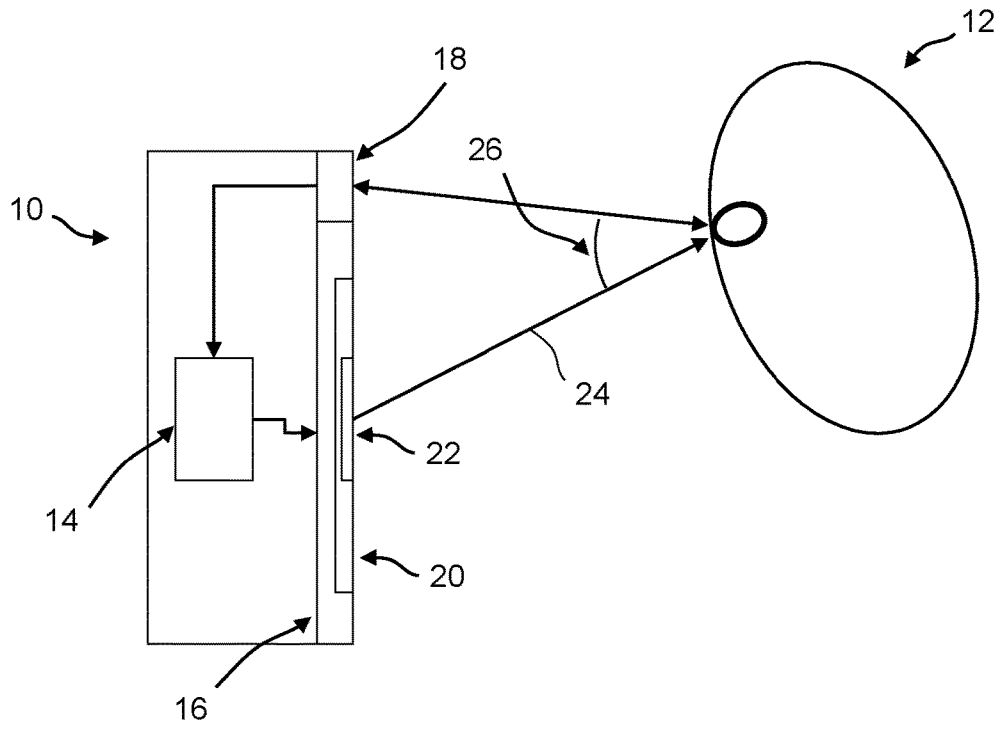
FIG. 1 is a graphical representation of a device for determining an indication of an acuity level of a user.

In the following, the invention will be explained in more detail with reference to the accompanying figures. In the Figures, like elements are denoted by identical reference numerals and repeated description thereof may be omitted in order to avoid redundancies.

Figures 2A, 2B:
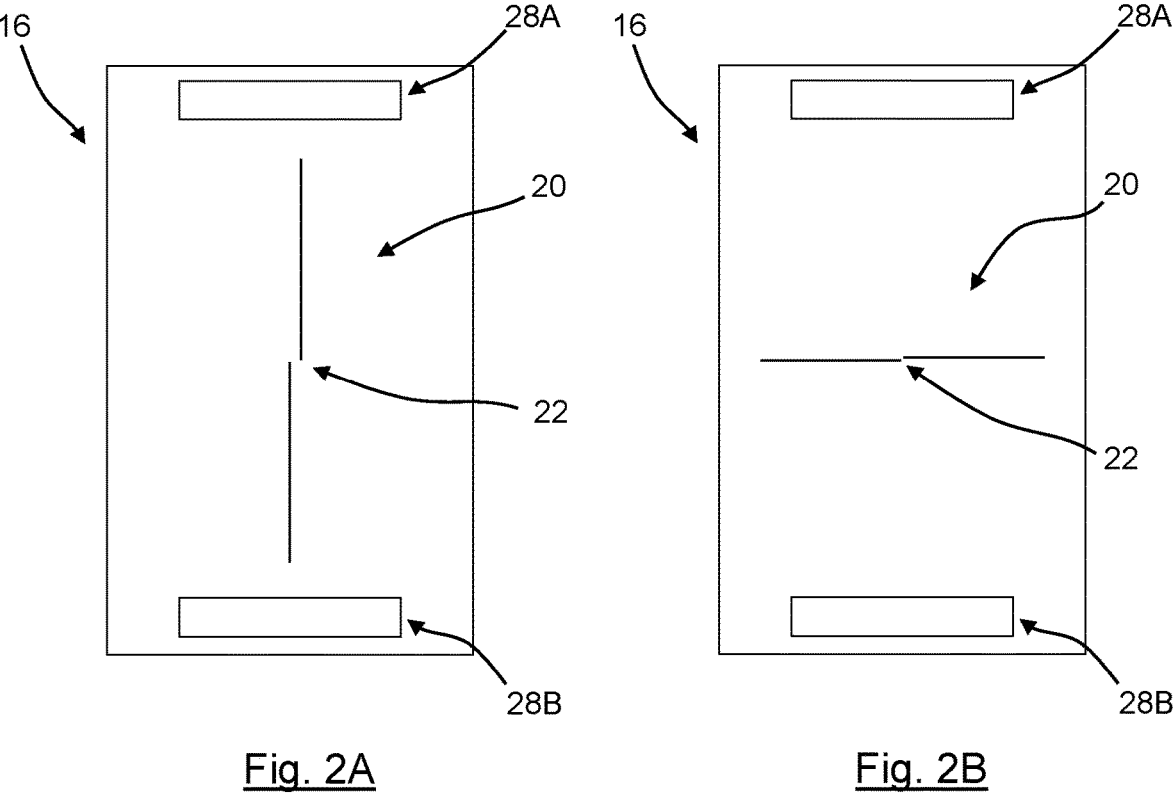
FIGS. 2A and 2B are a schematic depiction of a display displaying a graphical representation with a discontinuity in different orientations.

As shown in FIGS. 2A and 2B, a graphical representation 20 on a display 16 may be displayed in different orientations, e.g. during different phases of the optical acuity test. Accordingly, as shown in FIG. 2A, the graphical representation 20 and the discontinuity 22, which are depicted here as a variant of a Vernier acuity test, are aligned along a longitudinal direction or axis of the display 16, such that the lines form an extension of each other and are separated only by a discontinuity 22, e.g. in a staggered manner with a particular offset or gap. Although the user may be prompted to rotate the device so as to rotate the display, the orientation of the graphical representation 20 may also be automatically altered by a rotation of 90 degrees, as shown in FIG. 2B, such that the orientation of the graphical representation 20 is perpendicular to the longitudinal direction of the display 16. In other words, while the acuity test may be performed in an upright or vertical orientation, the acuity test may switch to a laterally extending or essentially horizontal orientation, so as to provide a variation in the acuity test and to provide different testing aspects.

Furthermore, the acuity test comprises indications 28A, 28B, arranged at opposing ends of the graphical representation 20 whereas in the case of a horizontal or perpendicular orientation of the graphical representation 20 the indications 28A, 28B are arranged at opposing ends of the display 16 in a longitudinal direction. The indications 28A, 28B enable that a user may provide a user response, wherein the indications 28A, 28B indicate whether the user perceives the graphical representation 20 as continuous or discontinuous, respectively. To select the respective indication 28A, 28B, the display 16 according to a preferred embodiment is configured as a touch screen, wherein a user may tip at the respective region of the display 16 or may swipe e.g. from a central position of the display 16 to the respective indication 28A, 28B.

To further increase the variation and accuracy level of the acuity corresponding with the discontinuity, the control unit implements an anti-aliasing technique, as schematically depicted in FIGS. 3A and 3B. Accordingly, as described in the above, pixels may not only be presented in a black or white color, as depicted in FIG. 3A, but may essentially comprise any particular grayscale color therein between, such that a gradient shift may be performed, as shown in FIG. 3B. In this example, the previously black pixel is reduced to e.g. 90 percent intensity and wherein an adjacent white pixel is increased to a black pixel intensity having e.g. a 10 percent pixel intensity. Thereby, a full pixel shift is not provided, yet a user may or may not perceive the gradient shift as a traversing pixel.

Accordingly, the magnitude and resolution of discontinuity may not be limited by the number of pixels, but may be further increased using the gradient shift provided by the anti-aliasing technique, such that the acuity level of a user may be determined with higher accuracy. Thereby, the accuracy and detail level of the acuity test may be further increased, such that support for medically significant acuity levels may be provided that were previously not identifyable using a standard display and using full pixel shifts. For example, potentially depending on the available resolution, LogMAR shifts up to −0.7 or higher may be obtained.

In FIG. 1 a graphical representation of a device 10 for determining an indication of an acuity level of a user 12 is schematically depicted. The device 10 according to this example is a hand-held device in the form of a mobile terminal and is configured to perform an optical acuity test. In order to do so, the device 10 comprises a control unit 14, which is in communication with a display 16 so as to provide control or display signals to said display 16 to output and display an optical acuity test to the user 12. The optical acuity test may e.g. be embedded on a storage medium of the device in the form of executable instructions.

The control unit 14 may e.g. be provided as a micropro-cessor embedded on a chip of the mobile terminal and may be configured to process and evaluate a plurality of received signals. Amongst these signals and according to a preferred embodiment are signals received from an optional optical sensor 18, which is integrated in the device at a front side and is arranged in proximity or is adjacent to the display 16. The optical sensor 18 according to the present example is part of an integrated camera of the device and is configured to detect optical signals.

Accordingly, the control unit 14 may determine or detect one or more facial characteristic of the user 12 by means of the optical sensor 18 of the device 10. For example, a particular feature such as the eyes, nose, or overall shape using feature recognition may be determined based on the received optical signals. However, the optical sensor 18 and/or control unit 14 may also be configured to determine the presence of facial characteristics based on detected signals indicating a particular distance range, e.g. between 20 cm and 70 cm, a contrast level, and/or an object size. Accordingly, a facial structure or characteristic is not directly identified, but is determined based on e.g. a par-ticular contrast difference of an object being in the proximity of the optical sensor 18. Using the optical signals, the control unit 14 may then determine a distance 24 between the display 16 and the face of the user 12.

By knowing the distance 24 between the display 16 and the user 12 the control unit 14 may accordingly adjust the optical acuity test. When performing the optical acuity test, the user 12 is presented with a number of graphical repre-sentations 20, which are displayed on the display 16. Each graphical representation 20 comprises a discontinuity 22, which is preferably present in a center region of the display 16, as indicated in FIG. 3. This has the advantage that the distance 24 between the user 12 and the display 16 corre-sponds to a distance 24 between the discontinuity 22 and the user 12, such that a primary focus lies on the discontinuity 22.

Based on the optionally determined distance 24, the control unit 14 may then adjust a size or extension of the displayed graphical representation 20, such that the user 12 perceives the same appearance of the graphical representa-tion 20 and discontinuity 22 at varying distances. Thereby, a user 12 is provided with improved test conditions, which may be essentially the same during the performance of the acuity test and between acuity tests performed at different time points. Although a warning signal may be output, either additionally or alternatively, to indicate that a user is moving out of a preferred range, such adaptation avoids that a user 12 accidentally comes into closer proximity with the dis-continuity 22 or is at a distance 24 rendering it more difficult to identify the discontinuity 22. Accordingly, the validity of the indication of the acuity level determined by performing the acuity test is increased.

The adjustment of the graphical representation 20 is furthermore performed based on a resolution of the display 16, such that the pixel density and the size or dimensions of the display 16 are taken into account. Thereby, the test may be performed with a similar accuracy between devices having a different resolution as the user is always presented with a graphical representation having a similar size and extension.

The control unit 14 may furthermore optionally determine an interaction angle 26 of the user 12 with the device 10 or display 16. Based on the determined angle 26, the control unit 14 may adjust the displayed optical acuity test by adjusting a displayed perspective of the graphical representation 20 according to the determined angle 24, wherein the extension of the displayed acuity test may be accordingly adjusted. Hence, when a user 12 tilts the device 10, the displayed acuity test may have an essentially stationary appearance, such that the user 12 always perceives the displayed acuity test in essentially the same manner.

In addition, as described in the above, the optical sensor 18 may provide data regarding to ambient conditions such as hue and brightness and the control unit 14 may hence also be configured to adjust e.g. a luminosity, contrast, and/or hue of the display 16 so as to take varying ambient conditions into account and to ensure that an appearance of the displayed acuity test to a user 12 is hence essentially the same under varying ambient conditions.

Accordingly, using the control unit 14 and the optical sensor 18, an improved stability of the testing conditions may be provided, such that the acuity test may be performed essentially under standardized conditions.

Figure 5:
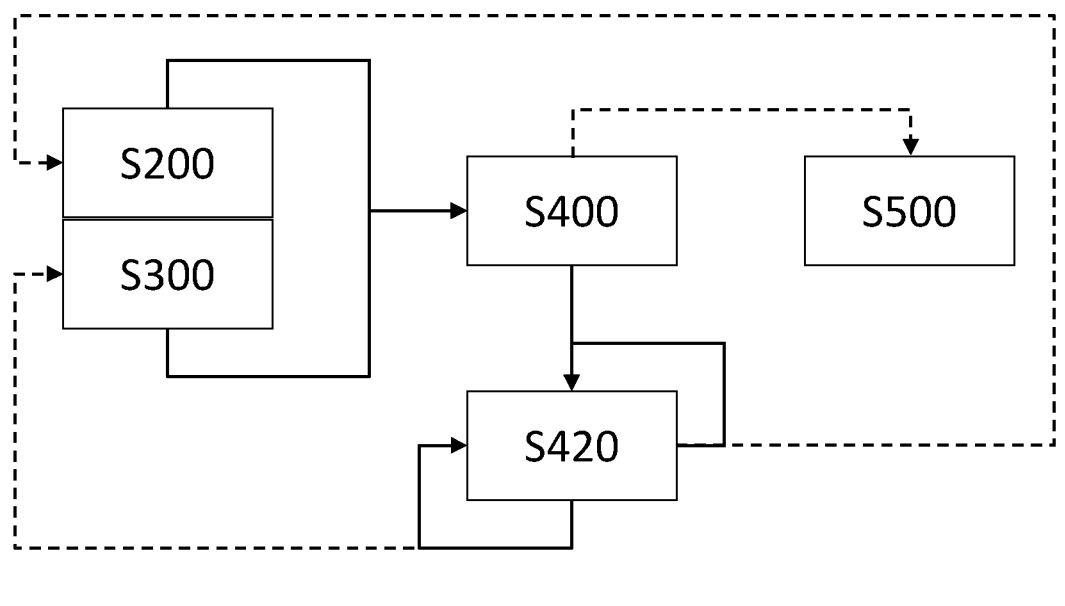
FIG. 5 schematically depicts steps for determining an indication of a final acuity level according to a second step of an optical acuity test.

The optical acuity test that may be performed on the device as part of a computer implemented method is further described in the exemplary embodiments according to FIGS. 4 and 5, which depict a first and second method step to determine an indication of an initial acuity level and a more refined indication of a final acuity level, respectively.

Accordingly, as schematically depicted in FIG. 4, a user may be provided with a graphical representation comprising a discontinuity according to a first acuity level being displayed on a display in step S100. Furthermore, the display indicates that a user response request is required by selection of an indication as to whether the user perceives the graphical representation as being continuous or being discontinuous.

If the user response correctly identifies the discontinuity, as indicated with the arrowhead originating from the bottom of step S100, the control unit adjusts the acuity test by displaying on the display a further graphical representation comprising a discontinuity corresponding to a second acuity level in step S110 and prompting the user to identify said discontinuity by providing a user response, wherein the second acuity level is higher than the first acuity level.

If the user again correctly identifies the discontinuity according to the second acuity level, the method may proceed to step S112, wherein the method performs the step of adjusting the acuity test by displaying, using the control unit, on the display a further graphical representation comprising a discontinuity corresponding to an acuity level being higher than the previous acuity level with a predefined amount, and prompting the user to identify said discontinuity by providing a user response.

Said step may be repeated until a predefined maximum acuity level is achieved, which is controlled in step S114, as indicated by the dashed line. If the maximum acuity level is achieved, the method may resolve an initial acuity level corresponding to the maximum acuity level in step S200.

The subsequent displaying of graphical representations with discontinuities corresponding to increasing acuity levels is furthermore also stopped, when the user does not identify the second or subsequent discontinuity, as indicated with the arrowheads originating from the right side of the respective steps. The method then continuous at step S116, wherein a further graphical representation is displayed comprising a discontinuity corresponding to an acuity level being lower than the previous acuity level with a predefined amount and prompting the user to identify said discontinuity by providing a further user response.

The user may then either correctly identify the discontinuity, such that the method may proceed to step 116A and performs the step of adjusting the acuity test by displaying a further graphical representation comprising a discontinuity corresponding to an acuity level being higher than the previous acuity level with a predefined amount and prompting the user to identify said discontinuity by providing a further user response, wherein, if the further user response identifies the discontinuity, said step is repeated until a discontinuity is not identified, as depicted with the arrowhead originating from the right side of step S116A, or until the maximum acuity level is achieved, as indicated with the dashed line, wherein the indication of the initial acuity level is set to the acuity level corresponding to the last displayed discontinuity in step S200.

Should the user not identify the discontinuity at step S116, said step is repeated in step S116B until a discontinuity is correctly identified, as indicated with the arrowhead originating from the bottom from S116B, until the first acuity level displayed in step S100 is achieved, or until a total of two discontinuities, preferably subsequently, have not been identified, wherein the indication of the initial acuity level is set to the acuity level corresponding to the last displayed discontinuity in step S200.

Thereby, whereas steps S110 to S114 may provide graphical representations with larger differences in acuity levels in the respective discontinuities, steps S116, S116A, and S116B provide a more defined estimate or finetuning of the rough estimate.

Should the user not be able to identify the discontinuity according to the first acuity level in step S100, as indicated with the arrowhead originating from the right side of S100, the method chooses a predefined lower limit as the acuity level in step S120 and sets the initial acuity level to said limit in step S200.

In the second step of the method, which is schematically depicted in FIG. 5, a further finetuning of the indication of the initial acuity level resolved in step S200 is performed so as to resolve an indication of a final acuity level in step S500.

Accordingly, a pool of graphical representations is generated in step S400, wherein each graphical representation comprises a discontinuity corresponding to a specific acuity level, wherein the pool comprises a predefined number of graphical representations having a discontinuity according to the indication of the initial acuity level S200 and wherein furthermore a predefined number of graphical representations having a discontinuity corresponding to an acuity level being, in a preferred embodiment, higher or, alternatively, lower than the indicated initial acuity level S200 with a predefined amount is added in step S300. The addition of these further graphical representations, in one example, may be based on an evaluation of user responses and the number of identifications for the graphical representations having the discontinuity corresponding to the indication of the initial acuity level. For example, when two out of three or a majority of user responses correspond to a correct identification, the additional graphical representations may have a discontinuity corresponding to an acuity level being higher than the indicated initial acuity level S200 whereas in the opposite situation this acuity level is lower. Such pre-evaluation is, however, merely optional. In a preferred embodiment, a predefined number of graphical representations having a discontinuity according to the indication of the initial acuity level S200 and a predefined number of graphical representations having a discontinuity corresponding to an acuity level being higher is added in step S300, either depending on such pre-evaluation or by standard.

As described in the above, the indication of the initial acuity level resolved in step S200 may be represented by a corresponding LogMAR value of e.g. –0.4, wherein, for example, three representations according to said LogMAR value may be added to the pool and a further three representations according to a LogMAR value of e.g. –0.5 may be added to the pool, i.e. optionally when the majority of the previous user responses with regard to the graphical representations corresponding to the indication of the initial acuity level are correct, so as to generate a pool having six graphical representations in step S400.

The acuity test and the pool are then adjusted in step S420 by displaying, a randomly selected graphical representation from said pool, wherein the displayed graphical representation is removed from the pool and wherein the user is prompted to identify the corresponding discontinuity.

If the user correctly identifies the discontinuity, a predefined number of graphical representations having a discontinuity corresponding to an acuity level being higher than the initial acuity level with a predefined amount, e.g. a LogMAR value of –0.1, may be added to the pool, if a graphical representation having a discontinuity corresponding to the resulting acuity level has not yet been added to the pool. For example, when a user correctly identifies a discontinuity according to the acuity level of –0.5 LogMAR after the initial pool generation, at a start of the second step and as indicated with the dashed line originating from the bottom of step S420 and connecting to the step of adding graphical representations in step S300, a corresponding number of graphical representations with a higher acuity level of e.g. –0.6 LogMAR are added to the pool.

In contrast, should the user not identify the discontinuity, a predefined number of graphical representations having a discontinuity corresponding to an acuity level being lower than the initial acuity level with a predefined amount may be added to the pool, if a graphical representation having a discontinuity corresponding to said acuity level has not yet been added to the pool, for example, when a user does not identify a discontinuity according to a graphical representation according to the indication of the initial acuity level, as indicated with the dashed line originating from the right side of step S420 and connecting to the step of adding the graphical representations in step S300. Following this example, a corresponding number of graphical representations with a lower acuity level of e.g. –0.3 LogMAR are added to the pool These steps are continued and the user responses are registered until the pool is empty at step S500, wherein an indication of a final acuity is resolved based on the user responses, for example, by evaluating the user responses and determining the highest acuity level for which a majority of the user responses correctly identified the corresponding discontinuity. Alternatively, or in addition, a statistical analysis and/or averaging of a corresponding score defined by the respective user responses and corresponding acuity levels may be performed. The second step of the method hence provides an indication of a final acuity level, such that the indication of the initial acuity level is refined and/or confirmed and an initial estimate of the acuity level may be more exactly determined and fine-tuned. Thereby, a physician may be supported in assessing the acuity level of a patient and performing a diagnosis.

Although not depicted in FIGS. 4 and 5, it may further be provided that the user responses, scoring, indication of the initial acuity level, and/or indication of the final acuity level are stored and/or transmitted to a medical professional so as to obtain a tracking and monitoring of the development of the acuity level or test performance of the user or patient. Thereby, in particular since the method facilitates performing the acuity test at any location and at a regular or periodic interval and/or according to a prescribed test regimen, any significant changes may be detected at an early stage without requiring the user to attend a medical practice.

It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the invention.

LIST OF REFERENCE NUMERALS

10 Device
12 User
14 Control unit
16 Display
18 Optical sensor
20 Graphical representation
22 Discontinuity
24 Distance
26 Angle
28A,B Indication
S100 Displaying first acuity level
S110—
S120 Determining indication of initial acuity level
S200 Initial acuity level or adding corresponding graphical representations
S300 Adding further graphical representations
S400 Generating pool
S420 Adjusting pool
S500 Resolving indication of final acuity level

The invention claimed is:

1. A computer implemented method for determining an indication of an acuity level of a user, comprising the steps of:

selecting an optical acuity test using a control unit in communication with a display of a device, wherein the display has a predefined resolution; and causing the device to display the optical acuity test on the display of the device, wherein the displayed optical acuity test comprises a graphical representation and prompts the user to provide a user response indicative of a gradient shift and/or pixel positioning in the graphical representation, receiving the user response, the user response indicative of the gradient shift and/or pixel positioning in the graphical representation;

receiving optical sensor data indicative of a distance between a facial characteristic of the user and the device; and generating an adjusted optical acuity test based on the user response, the optical sensor data, and the predefined resolution of the display, wherein the optical acuity test corresponds to a first Logarithm of the Minimum Angle of Resolution (LogMAR) value and the adjusted optical acuity test corresponds to a second LogMAR value that is higher than the first LogMAR value if the user response fails to satisfy a threshold value.

2. The method according to claim 1, wherein the prompt instructs the user to identify a discontinuity in the graphical representation and the discontinuity is aligned along a longitudinal direction of the display and wherein a user response is received by the control unit by a selection of an indication relating to the discontinuity, wherein the graphical representation comprises the indication on opposing ends of the graphical representation.

3. The method according to claim 2, wherein the display is configured as a touchscreen and the user response is received by the control unit by means of a tactile interaction with the touchscreen at or in a direction of a region of the display corresponding to the indication.

4. The method according to claim 2, wherein the graphical representation comprises at least two lines essentially arranged along a longitudinal direction of the display and wherein the discontinuity is formed as an offset of said lines in a direction perpendicular to the longitudinal direction of the display.

5. The method according to claim 1, wherein an indication of the acuity level of the user is determined using the control unit and based on the user response.

6. The method according to claim 1, wherein the acuity test is performed by the control unit in two steps, wherein, in the first step, an indication of an initial acuity level is determined and, in the second step, said indication of the initial acuity level is refined and/or confirmed as an indication of a final acuity level.

7. The method according to claim 6, wherein, in the first step, the graphical representation comprises a discontinuity corresponding to a first acuity level, wherein if the user response correctly identifies the discontinuity, the control unit adjusts the acuity test by displaying on the display a further graphical representation comprising a discontinuity corresponding to a second acuity level and prompting the user to identify said discontinuity by providing a user response, the second acuity level being higher than the first acuity level, and wherein if the user response does not identify the discontinuity, the control unit sets the indication of the initial acuity level to a predefined initial acuity level being lower than the first acuity level.

8. The method according to claim 7, wherein, if the user response correctly identifies the discontinuity according to the second acuity level, the method further comprises performing the step of adjusting the acuity test by displaying, using the control unit, on the display a further graphical representation comprising a discontinuity corresponding to an acuity level being higher than the previous acuity level with a predefined amount and prompting the user to identify said discontinuity by providing a user response, wherein said step is repeated until a predefined maximum acuity level is achieved, if the user response correctly identifies the discontinuity, thereby achieving the indication of the initial acuity level, or until the user response does not identify the discontinuity.

9. The method according to claim 8, wherein, if the user response does not identify the discontinuity, the method further comprises performing the step of adjusting the acuity test by displaying, using the control unit, on the display a further graphical representation comprising a discontinuity corresponding to an acuity level being lower than the previous acuity level with a predefined amount and prompting the user to identify said discontinuity by providing a further user response, wherein:

if the further user response does not identify the discontinuity, said step is repeated until a discontinuity is correctly identified, until the first acuity level is achieved, or until a total of two subsequent discontinuities have not been identified, wherein the indication of the initial acuity level is set to the acuity level corresponding to the last displayed discontinuity; or if the further user response identifies the discontinuity, the method further comprises performing the step of adjusting the acuity test by displaying, using the control unit, on the display a further graphical representation comprising a discontinuity corresponding to an acuity level being higher than the previous acuity level with a predefined amount and prompting the user to identify said discontinuity by providing a further user response, wherein, if the further user response identifies the discontinuity, said step is repeated until a discontinuity is not identified or until the maximum acuity level is achieved, wherein the indication of the initial acuity level is set to the acuity level corresponding to the last displayed discontinuity.

10. The method according to claim 6, wherein, in the second step, a pool of graphical representations is generated, each graphical representation comprising a discontinuity corresponding to a specific acuity level, said pool comprising a predefined number of graphical representations having a discontinuity according to the indication of the initial acuity level and further comprising a predefined number of graphical representations having a discontinuity corresponding to an acuity level being higher or lower than the initial acuity level with a predefined amount, wherein the acuity test is adjusted by displaying, using the control unit, on the display a randomly selected graphical representation from said pool and prompting the user to identify said discontinuity, wherein the method comprises the steps of:

adding a predefined number of graphical representations having a discontinuity corresponding to an acuity level being higher than the indication of the initial acuity level with a predefined amount, if the further user response identifies the discontinuity and if a graphical representation having a discontinuity corresponding to said acuity level has not yet been added to the pool and does not exceed a predefined amount from the indication of the initial acuity level; and/or adding a predefined number of graphical representations having a discontinuity corresponding to an acuity level being lower than the initial acuity level with a predefined amount or equal to the initial acuity level, if the further user response does not identify the discontinuity and if a graphical representation having a discontinuity corresponding to said acuity level has not yet been added to the pool and does not exceed a predefined amount from the indication of the initial acuity level, wherein the graphical representations are subsequently displayed and each displayed graphical representation is removed from the pool after a user response has been received, and wherein the indication of the final acuity level is determined based on the user responses.

11. The method according to claim 10, wherein the indication of the final acuity level is determined after the pool comprises no further graphical representations, wherein the indication of the final acuity level corresponds to the last correctly identified highest acuity level or wherein the indication of the final acuity level is determined as the highest acuity level for which a majority of the user responses corresponds to an identification of the discontinuity.

12. The method according to claim 10, wherein the generation of the pool includes evaluating user responses of the predefined number of graphical representations having a discontinuity according to the indication of the initial acuity level, wherein the further predefined number of graphical representations have a discontinuity corresponding to an acuity level being higher than the indication of the initial acuity level with a predefined amount, if a majority of the user responses corresponds to an identification of the discontinuity, or to an acuity level being lower than the indication of the initial acuity level with a predefined amount, if a majority of the user responses does not correspond to an identification of the discontinuity.

13. The method according to claim 6, wherein the alignment of the graphical representation is switched to an alignment being perpendicular to the longitudinal direction or wherein the device is rotated from an upright position to a laterally extending position, when the second step is performed.

14. The method according to claim 1, wherein the displayed optical acuity test comprises or essentially consists of the graphical representation displayed in black color on a white background.

15. The method according to claim 1, wherein the displayed optical acuity test comprises at least two lines and wherein the adjust ed optical acuity test includes adjust ed size, length, and/or thickness of said lines.

16. The method according to claim 1, further comprising the step of detecting the facial characteristic of a user in the optical sensor data, wherein the control unit determines the distance between the display and the detected facial characteristic of the user based on the detected facial characteristic.

17. The method according to claim 16, wherein an angle between the display and the detected facial characteristic of the user is determined using the control unit and the adjusted optical acuity test is also generated based on the determined angle.

18. The method according to claim 1, wherein the adjusted optical acuity test is also generated based on an ambient brightness, contrast, and/or hue detected by an optical sensor of the device being in communication with the control unit.

19. The method according to claim 18, further comprising adjusting a luminosity, contrast, and/or hue of the display.

20. The method according to claim 19, wherein the adjustment is performed continuously or periodically.

21. The computer program product embodied on a computer readable storage medium and configured so as when executed on a processor to perform operations of the method according to claim 1.

22. The device for determining an indication of an acuity level of the user, comprising a control unit and a display, wherein the device is configured to perform the method according to claim 1.

23. The device according to claim 22, further comprising an optical sensor and configured to perform step of detecting at least a facial characteristic of a user by means of the optical sensor of the device being in communication with the control unit.

24. The device according to claim 22, wherein the device is configured as a portable and/or hand-held device.

25. The device according to claim 24, wherein the device is configured as a mobile terminal and comprising an integrated camera as an optical sensor.

26. The device according to claim 22, wherein the device comprises a wireless communication module and wherein the control unit is configured to perform the optical acuity test using data received from said wireless communication module and/or to transmit the determined indication of the acuity level to a remote device using said wireless communication module.

27. The method according to claim 1, wherein the graphical representation comprises at least two lines essentially arranged along a longitudinal direction of the display and wherein the discontinuity is formed as an offset of said lines in a direction perpendicular to the longitudinal direction of the display and wherein an indication of the acuity level of the user is determined by using the control unit and based on the user response.

28. The method according to claim 27, wherein the adjusted optical acuity test is also generated based on a detected resolution of the display.

29. The method according to claim 27, wherein the offset is formed as a gradient shift of the one or more pixels using the anti-aliasing.

* * * * *